United States Patent [19]

Saleh et al.

[11] Patent Number: 4,831,164

[45] Date of Patent: May 16, 1989

[54] PROCESS OF PREPARING CARBOXYLIC ANHYDRIDE

[75] Inventors: Ramzi Y. Saleh, Neshanic Station; Israel E. Wachs, Bridgewater, both of N.J.

[73] Assignee: Exxon Chemical Patents Inc., Linden, N.J.

[21] Appl. No.: 180,061

[22] Filed: Apr. 11, 1988

Related U.S. Application Data

[60] Continuation-in-part of Ser. No. 102,164, Sep. 28, 1987, which is a division of Ser. No. 782,966, Oct. 2, 1985, Pat. No. 4,728,744.

[51] Int. Cl.$^4$ ............................................. C07D 307/89
[52] U.S. Cl. .................................. 549/239; 549/235; 549/236; 549/248; 549/256; 549/257; 549/258
[58] Field of Search ............... 549/235, 236, 239, 248, 549/256, 257, 258

[56] References Cited

U.S. PATENT DOCUMENTS

| | | | |
|---|---|---|---|
| 3,464,930 | 9/1969 | Friedrichsen et al. | 252/469 |
| 3,509,179 | 4/1970 | Friedrichsen et al. | 549/248 |
| 3,894,971 | 7/1975 | Reuter et al. | 549/248 X |
| 4,582,911 | 4/1986 | Wachs et al. | 549/239 |
| 4,582,912 | 4/1986 | Wachs et al. | 549/239 |
| 4,728,744 | 3/1988 | Saleh et al. | 549/239 |

FOREIGN PATENT DOCUMENTS 1237954 7/1971 United Kingdom .

OTHER PUBLICATIONS

Matsuda et al., Applied Catalysts, vol. 8, (1983), pp. 149–165.

Primary Examiner—Richard L. Raymond
Attorney, Agent, or Firm—D. E. Furman; J. J. Mahon

[57] ABSTRACT

In accordance with the process of this invention, an improved catalyst for molecular oxidation of hydrocarbons to form the corresponding carboxylic anhydrides is prepared by the steps of forming a catalyst precursor by depositing on titanium dioxide catalyst solids in the anatase form a continuous monolayer amount of at least one source of titanium oxide, calcining the thus-formed catalyst precursor under conditions sufficient to convert the titanium oxide source into the oxide form, depositing upon the calcined catalyst precursor a continuous monolayer amount of at least one vanadium compound which is convertible into vanadium oxide upon heating and calcining the vanadium-deposited solids under conditions sufficient to convert the vanadium compound into vanadium oxide.

12 Claims, 1 Drawing Sheet

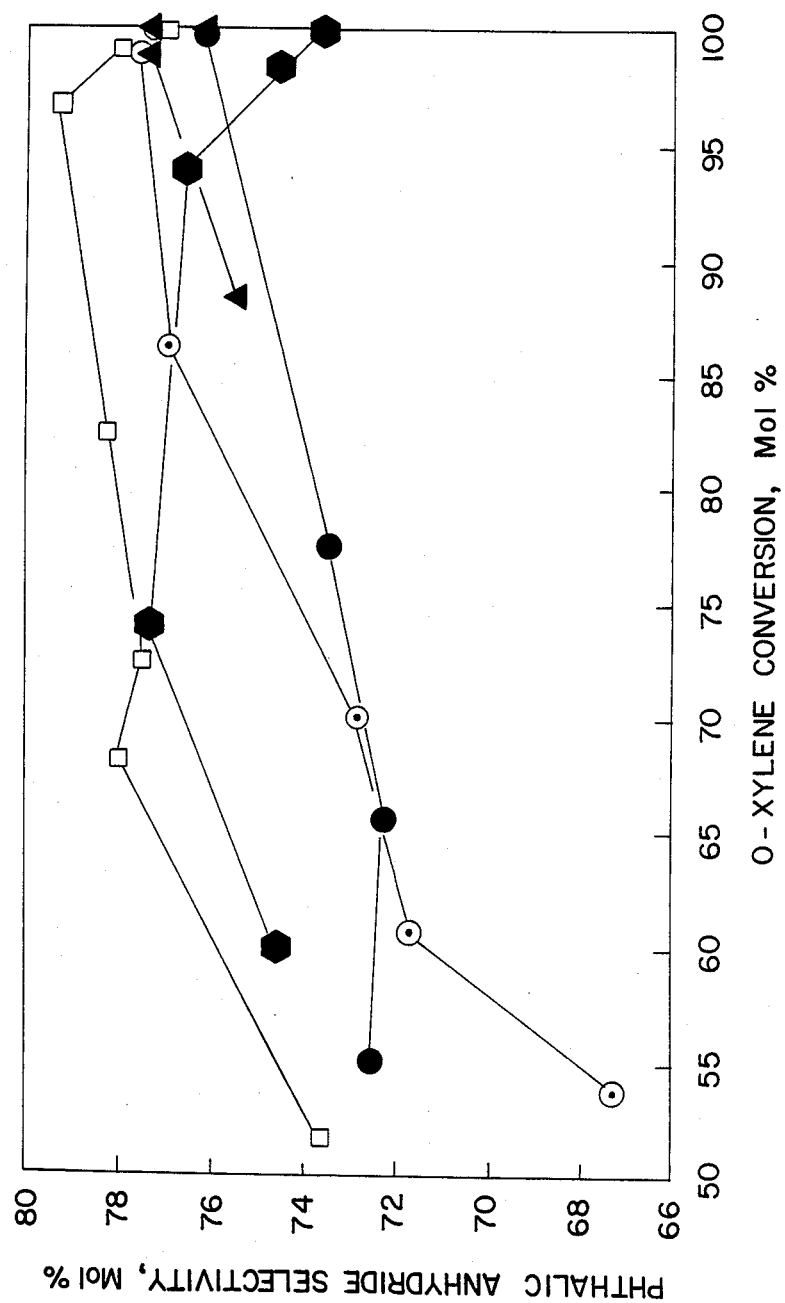

PROCESS OF PREPARING CARBOXYLIC ANHYDRIDE

CROSS-REFERENCE TO RELATED APPLICATION

This application is a continuation-in-part of pending application Ser. No. 102,164, filed Sept. 28, 1987, which is a divisional application of Ser. No. 782,966 filed Oct. 2, 1985, which issued as U.S. Pat. No. 4,728,744.

BACKGROUND OF THE INVENTION

This invention relates generally to the manufacture of carboxylic anhydrides, and more particularly to novel catalysts and methods for their use in manufacturing carboxylic anhydrides by molecular oxidation of hydrocarbon feedstocks, in particular the manufacture of phthalic anhydride by molecular oxidation of orthoxylene.

DESCRIPTION OF THE PRIOR ART

Carboxylic anhydrides are widely produced in large quantities through the molecular partial oxidation of hydrocarbon feedstocks, particularly phthalic anhydride from orthoxylene. The phthalic anhydride product is commercially useful for reactions with alcohols, such as oxo-alcohols to form the corresponding phthalic anhydride alcohol esters, which find use as plasticizers and lubricants.

Catalysts for the above partial oxidation, in which vanadium pentoxide is deposited on titania, are known in the art, for example, as disclosed in U.S. Pat. Nos. 3,909,457, 3,926,846 and 4,305,843.

See also S. Matsuda et al., *Applied Catalysis*, 8 (1983) 149-165, for discussion of titanium dioxide catalysts in general.

Commonly-assigned U.S. Pat. No. 4,582,911, which is hereby incorporated herein by reference, discloses a phthalic anhydride catalyst prepared by sequentially depositing on titanium dioxide solids in the anatase form a discontinuous monolayer of at least one source of tantalum oxide, calcining the thus-formed catalyst precursor under conditions sufficient to convert the tantalum oxide source into the oxide form, depositing upon the calcined catalyst precursor a catalytically effective amount of at least one vanadium compound which is convertible into vanadium oxide upon heating, and calcining the vanadium-deposited solids under conditions sufficient to convert the vanadium compound into vanadium oxide.

Commonly-assigned U.S. Pat. No. 4,582,912, incorporated herein by reference, discloses a phthalic anhydride catalyst prepared from sources of vanadium oxide, titanium oxide and the oxide of a promotor metal selected from Sb, Ga, Ge, In, Tl, Pb, Se, Te, P and Bi, also by a process of sequential deposition, in which there is first formed a calcined catalyst precursor comprising vanadium oxide on titanium oxide, and a vanadium oxide source and a reactive metal oxide source are thereafter co-deposited on the calcined catalyst precursor, the resulting catalyst then being calcined. It is noted at column 5, lines 6-12 that if vanadium oxide and a reactive metal oxide are co-deposited onto fresh titanium dioxide anatase, inferior catalyst performance results, compared with catalysts wherein the vanadium and reactive metal are sequentially deposited. It is further indicated that the titanium dioxide during the conventional preparation may have been incompletely covered with the vanadium monolayer, and that therefore the titanium dioxide surface was either exposed or otherwise adversely affected by the presence of the reactive metal surface species on the titania.

Commonly-assigned U.S. Pat. No. 4,728,744, which is also hereby incorporated by reference, discloses a sequential deposition process for forming a zirconia based catalyst wherein a source of zirconium oxide is deposited in an amount sufficient to provide a continuous monolayer on titanium dioxide solids in the anatase form; the thus-formed catalyst precursor is then calcined; and a source of vanadium oxide is then deposited on the calcined catalyst precursor; and the catalyst is again calcined.

In U.S. Pat. Nos. 3,464,930 (1969) and 3,509,179 (1970) and British Pat. No. 1,237,954 (1971) to BASF, oxidation catalysts containing V and Ti are disclosed in which the active catalyst components are deposited on nonporous, inert materials, e.g., porcelain, fused aluminum oxide, silicon carbide, or fused or sintered silicates. It is indicated that the carriers can be advantageously primed, precoated or pretreated, particularly when relatively porous, by contacting with one or more oxides of V, Mo, W, Cr, Ti or Fe, prior to coating the carrier with the active catalyst composition containing $V_2O_5$ and $TiO_2$. The said oxides or compounds of the metals which are converted into the oxides by heating are contacted with the carrier in a melt, or preferably in solution, to produce a uniform coating on the carrier. It is preferred to heat the carrier prior to coating, i.e. after priming, to a temperature of from about 300° C. to 1000° C. The V and Ti components are then simultaneously applied onto the carrier substrate.

U.S. Pat. No. 3,894,971 to BASF discloses a multilayer supported catalyst which contains in the active material from 60 to 99 percent by weight of titanium dioxide and/or zirconium dioxide, from 1 to 40 percent by weight of vanadium pentoxide and up to 6 percent by weight of combined phosphorus, in which from 0 to 0.3 percent by weight of phosphorus is in the outer layer and more than 0.3 percent up to 6 percent of phosphorus is in the remaining catalytic material. The catalyst is prepared by first depositing onto a support a vanadium/phosphorus compound in a slurry or paste with $TiO_2$ anatase or $ZrO_2$, followed by depositing the second vanadium/phosphorus compound layer.

The foregoing disclosures relate to treatment of the inert carrier and not the catalyst active layer. It is generally believed that the above-discussed "priming" or "pre-coating" operations are intended to form a barrier against the migration to the active catalyst surface of impurities such as potassium, which can be present in certain catalyst carriers. In U.S. Pat. No. 3,894,971, for example, the relatively higher content of phosphorous in the catalysts' first (inner) layer, adjacent to the carrier support, acts to react with any migrating potassium components of the carrier to prevent, or slow the rate of, the further migration of these impurities to the active catalyst surface and thereby avoid the adverse reaction selectivity consequences in the use of the catalyst to produce carboxylic acid anhydrides.

In U.S. Pat. No. 4,293,449 to Standard Oil, attrition resistant desulfurization catalysts are prepared by applying to a "partially wetted," inert core a high surface area ("HSA") support material which is specified to be in powder form, and drying and calcining the coated core, and then impregnating with catalytic elements.

Suitable core materials are said to include silica, alumina, silicon carbide, titania and zirconia. Suitable coating materials are said to include hydrated alumina, titanate or zirconate salts. The thus-formed catalysts are said to be resistant to the shrinkage associated with catalysts formed using slurried coatings.

SUMMARY OF THE INVENTION

In accordance with the process of this invention, an improved titania-based catalyst for molecular oxidation of a hydrocarbon to form the corresponding carboxylic anhydride is prepared by the steps of (a) forming a catalyst precursor by depositing on titanium dioxide solids in the anatase form a continuous monolayer amount of at least one source of titanium oxide, (b) calcining the thus-formed catalyst precursor under conditions sufficient to convert the titanium dioxide source into the oxide form, (c) depositing upon the calcined catalyst precursor a continuous monolayer amount of at least one vanadium oxide source which is convertible into vanadium oxide upon heating, and (d) calcining the vanadium-deposited solids under conditions sufficient to convert the vanadium oxide source into vanadium oxide.

It has been surprisingly found that sequentially depositing a titanium dioxide source onto the $TiO_2$ anatase prior to deposition of the vanadium oxide source thereon achieves surprisingly improved catalyst selectivity in the subsequent use of the catalyst for manufacture of carboxylic acid anhydrides, particularly phthalic anhydride.

BRIEF DESCRIPTION OF THE DRAWINGS

The FIGURE is a graphical plot of phthalic anhydride selectivities versus percent conversion of orthoxylene for the catalysts prepared and tested as described in Examples 1 and 2.

DETAILED DESCRIPTION OF THE INVENTION

This invention relates to an improved process for the manufacture of carboxylic anhydrides by catalytic oxidation of hydrocarbons and relates more particularly to an improved process for producing aromatic carboxylic anhydrides such as phthalic anhydride and pyromellitic dianhydride by reacting a mixture of an oxygen-containing gas and an aromatic hydrocarbon (such as orthoxylene or naphthalene) in vapor phase in the presence of a novel catalyst therefor.

Catalyst Preparation

The novel catalyst of this invention is prepared by a four-step procedure, in which there is first deposited on titanium dioxide catalyst solids in the anatase form, titanium oxide (e.g., $TiO_2$) or at least one source of titanium oxide which is convertible into titanium oxide upon heating [step (a)]; followed by calcining of this catalyst precursor to form a calcined catalyst precursor [step (b)]. The calcined catalyst precursor is then treated in a second deposition step with the selected amount of a vanadium oxide source, and, optionally, catalyst promoters [step (c)]; followed by calcining in a separate calcining step to obtain the desired carboxylic anhydride catalysts [step (d)].

Suitable sources of titanium oxide for deposition on the titanium dioxide catalyst solids are Ti compounds which are convertible to the oxide (i.e., to the dioxide) upon heating to the calcination temperatures in the first calcination step. Suitable Ti compounds include titanium dioxide, titanium sulfate, titanium halide (e.g., titanium chloride, titanium dichloride), titanium oxyhalide (e.g., titanium oxychloride), titanium hydroxide, and titanium carboxylates such as formate, tartrate, salicylate and oxalate, which can then become titanium dioxide at the calcining temperature. The titanium compounds most convenient for the catalyst preparation have the formula $Ti(OR)_4$, where R is $C_2H_5$, $C_3H_7$, $C_4H_9$, or $C_5H_{11}$, and titanium oxalate.

The selected titanium oxide source deposited on the titanium dioxide catalyst solids in step (a) described above can be dry mixed with the titanium dioxide catalyst solids or deposited on the solids from solutions or suspensions of the titanium oxide sources, for example, using aqueous or organic solvents. Illustrative organic solvents include formamide, diethyl acetamide, ammonium thiocyanate, molten urea or an alcohol. The solutions can be sprayed onto the titanium dioxide catalyst solids (for example, in a coating drum which has been preheated to from about 150° to about 450° C.) or impregnated thereon using conventional techniques.

If wet techniques are used to deposit the titanium oxide source, the wetted solids can then be conveniently dried in air (or under an inert atmosphere such as nitrogen) to at least partially remove the solvent prior to calcination. Drying can be achieved by exposing the catalyst precursor to air at room temperature for a period of from about 1 to about 100 hours or by placing it in a forced hot air oven maintained at a temperature of less than about 180° C., typically between about 60° and about 150° C. for about 1 to about 16 hours. Alternatively, the precursor can be air dried at room temperature for between about 1 and about 48 hours and then placed in the forced hot air oven. Drying of the catalyst precursor preferably should be conducted at temperatures below which crystal phase transitions occur and until a level of nearly constant weight is achieved. Drying under reduced pressure at room or elevated temperature, as described above, can also be employed as a suitable alternative.

The thus-formed catalyst precursor is then, according to the process of this invention, calcined under conditions sufficient to convert the titanium oxide source into the oxide form (e.g., $TiO_2$) and to cause the titanium oxide to be strongly attached to the surface of the underlying titanium dioxide catalyst solids. Generally, a temperature of from about 100° to about 750° C. will be sufficient, and temperatures of from about 300° to about 600° C. are preferred, and the time of calcination will range generally from 0.5 to 16 hours, with a time of from about 1 to about 5 hours being preferred. The precise temperature and time of calcination will depend upon the particular titanium oxide source which has been selected for use, and should be such as to avoid substantial crystal phase transformations of the underlying titanium dioxide anatase into another crystalline form, e.g., rutile.

The calcination can be performed, as is preferred, in air or in the presence of an $O_2$-containing gas. Although not essential, it is desirable to maintain a steady flow of the chosen atmosphere over the catalyst precursor surface during calcination. Flow rates typically will be sufficient to provide a contact time with the catalyst of about 1 to about 10, preferably from about 1 to about 5, and most preferably from about 1 to about 3 seconds. Thus, suitable flow rates or space velocities of the calcining atmosphere may be manipulated by one skilled in the art to achieve the desired contact time.

The titanium oxide (e.g., $TiO_2$) which is employed as the titanium dioxide catalyst solids, is preferably in the anatase form. Preferably at least about 25 wt % (and most preferably from about 50 to about 100 wt %) of the titanium oxide is in the anatase form. The titanium oxide may be prepared by any conventional technique, for example the techniques described in R. J. H. Clark, "The Chemistry of Titanium and Vanadium", p. 267 (Elsevier Publishing Co., 1968).

The titanium oxide used in the catalyst of this invention is composed of substantially porous particles of a diameter of from about 0.4 to 0.7 micron and is preferably of a specific surface area of from 1 to 25 $m^2/g$, and more preferably of from about 2 to about 10 $m^2/g$, which are essentially aggregated masses of primary particles.

The particle diameter of the primary particles can be measured by a mercury penetration-type porosimeter. When using porous titanium oxide consisting of primary particles having a particle diameter in the range of 0.005 to 0.05 micron, the concentration of the slurry is from about 5 to 25% by weight, preferably from about 10 to 20% by weight. When using porous titanium oxide consisting of primary particles having a particle diameter of 0.05 to 0.4 micron, the slurry concentration is from about 10 to 40% by weight, preferably from about 15 to 25% by weight.

Depending upon the raw ore, $TiO_2$ may include iron, zinc, aluminum, manganese, chromium, calcium, lead, silicon, etc. These incidental elements are not detrimental to the reaction if their total amount is less than about 0.5% by weight based on $TiO_2$. Therefore, the $TiO_2$ can comprise pigment grade anatase, and no special purification procedure is required.

It has been found that improved o-xylene selectivities and yields are obtained when a continuous monolayer of titanium oxide (e.g., $TiO_2$) is present on the titanium dioxide catalyst solids. Therefore, the quantity of the titanium oxide source which is contacted with the titanium dioxide catalyst solids should be sufficient to provide a continuous monolayer of $TiO_2$ on the titanium dioxide catalyst solids.

In order to form a continuous monolayer on the titanium dioxide catalyst solids, the selected Ti oxide source will be provided in an amount sufficient to provide from about 0.1 to 10 wt. % of titanium oxides, calculated as $TiO_2$, deposited on the titanium dioxide solids, and the mole ratio of titanium present as a monolayer on the titanium dioxide catalyst solids, to the titanium in the titanium dioxide catalyst solids, is preferably from about 0.001 to about 0.111, and more preferably from about 0.003 to 0.053, gram atoms of titanium in the monolayer to gram atoms of titanium in the titanium dioxide catalyst solids.

Not every titanium dioxide catalyst solids particle need be individually treated to form thereon a continuous $TiO_2$ monolayer, and it can be understood that at least a majority (and most usually at least 90%) of the support particles will be characterized by a continuous $TiO_2$ monolayer when the solids sample is treated as described herein, particularly when using solution impregnation methods.

Without being bound thereby, it is believed that deposition of a continuous monolayer of titanium oxide source on the titanium dioxide catalyst solids alters the solids surface (perhaps by locking up titanium dioxide solids surface defects) and thus maximizes the subsequent interaction between vanadia and the titania.

The intermediate calcining step, in preparing the catalyst precursor, is believed to be necessary in order to cause the Ti oxide to form the necessary bond with the titanium dioxide solids surface. It is believed that the selected Ti oxide source is adsorbed (physically or both physically and chemically) onto the surface of the $TiO_2$ and that the calcining step converts the Ti oxide source to the oxide (e.g., $TiO_2$) which is chemically adsorbed on the titanium dioxide solids surface.

The resulting calcined catalyst precursor is then treated to deposit thereon a source of vanadium oxide (optionally co-deposited with a reactive metal source, as disclosed in U.S. Pat. No. 4,582,912), followed by calcining in a separate step.

The valence of the vanadium oxide source may vary, although the pentavalent state is preferred. The vanadium oxide source may be vanadium pentoxide but is preferably a vanadium compound such as ammonium metavanadate, vanadyl sulfate, vanadyl halide (e.g., vanadyl chloride, vanadyl dichloride), vanadyl oxyhalide (e.g., vanadyl oxychloride), vanadium hydroxide, and vanadyl carboxylates such as formate, tartrate, salicylate and oxalate, which can then become vanadium oxide at the calcining temperature. The vanadium compounds most convenient for the catalyst preparation are $V_2O_5$ and vanadyl oxalate.

The selected vanadium oxide source can be deposited on the calcined catalyst precursor from solutions or suspensions of the vanadium oxide source, for example using aqueous or organic solvents. Illustrative organic solvents include formamide, diethyl/acetamide, ammonium thiocyanate, molten urea or an alcohol. The solutions can be sprayed onto the calcined catalyst precursor solids (for example in a coating drum which has been preheated to from 150° to 450° C.) or impregnated thereon using conventional techniques.

If wet techniques are used, the wetted solids can then be dried in air or under an inert atmosphere (such as nitrogen) as described previously, conveniently at a temperature of from 50° to 200° C. followed by calcining for activation of the catalyst at a temperature of from 100° to 650° C., preferably 350° to 550° C., for about 0.5 to 16 hours, preferably 1 to 5 hours. The precise conditions of calcining will vary depending upon the vanadium oxide source which is employed, and should be sufficient to convert the vanadium compound into vanadium oxide. Again, the conditions of calcining should be such as to avoid substantial crystal phase transformations of the $TiO_2$ anatase into another crystalline form, e.g., rutile.

The thus-prepared catalyst will generally contain from about 0.7 to 50 wt. % of vanadium oxides, calculated as $V_2O_5$, and the mole ratio of vanadium to titanium present in the calcined catalyst is preferably from about 0.003 to 0.44, and preferably from about 0.008 to 0.08, of gram atoms of vanadium (calculated as V) per gram atom of titanium (calculated as Ti).

The precise quantity of the selected V source which is used in the V deposition step can therefore vary but preferably should be sufficient to provide full coverage of the $TiO_2$ surface, that is, to provide at least a continuous monolayer amount of the $V_2O_5$ on the $TiO_2$ surface of the calcined catalyst precursor. The minimum quantity of $V_2O_5$ to be provided, as calculated based on (1) the specific surface area of the $TiO_2$ (as conventionally determined by wet chemical analysis and BET surface area determinations), and (2) the cross-sectional area of $V_2O_5$ atoms relative to the surface density of the calcined catalyst precursor. As used herein, a "continuous monolayer amount" of $V_2O_5$ is defined to be the amount "$N_{min}$" as determined by the following expression (I):

$$N_{min} = (G) \times (A) \times (k) \qquad (I)$$

wherein "G" is the grams of the calcined catalyst precursor to be treated, "A" is the specific surface area in $m^2/gm$ (BET surface area) of the catalyst precursor, "$N_{min}$" is the weight in grams of $V_2O_5$ to be employed and "k" is the number of grams of $V_2O_5$ required to form a continuous monolayer of $V_2O_5$ on 1 gram of calcined catalyst precursor having a specific surface area of 1 $m^2/gm$. For a calcined catalyst precursor having a specific surface area of from 1 to 25 $m^2/gm$, the value "k" in the above expression is 0.0007. Therefore, expression (I) reduces to:

$$N_{min} = (G) \times (A) \times (0.0007) \qquad (II)$$

for a calcined catalyst precursor having a specific surface area of from 1 to 25 $m^2/gm$.

The grams of the selected V oxide source (calculated as its $V_2O_5$ equivalent) employed in this invention will preferably comprise at least about 1.7 $N_{min}$, and more preferably from about 2.5 $N_{min}$ to 50 $N_{min}$ (wherein $N_{min}$ is calculated as in Expression II) in order to ensure complete coverage of the $TiO_2$ surface on the calcined catalyst precursor.

Of course, not every catalyst precursor particle need be individually treated to form thereon a continuous $V_2O_5$ monolayer, and it can be understood that at least a majority (and most usually at least 90%) of the titanium dioxide catalyst solids will be characterized by a continuous $V_2O_5$ monolayer when treated as described herein, particularly when using solution impregnation methods.

The presence of more than a monolayer of $V_2O_5$ can be observed by examining the $TiO_2$ catalyst surface for evidence of $V_2O_5$ crystallites, which are believed to comprise the $V_2O_5$ species which forms when $V_2O_5$ is used in excess of the $V_2O_5$ monolayer amount. Such a surface examination for $V_2O_5$ crystallites can be conducted using Laser Raman Spectroscopy, as described in F. Roozeboom et al., J. Phys. Chem., vol. 84, p. 2783, (1980).

The surface area of the activated unsupported catalyst can vary typically from about 1 to about 25 $m^2/g$.

Surface areas herein are determined by the BET method, the general procedures and theory for which are disclosed in H. Brunaur, P. Emmett and E. Teller, *J. of Am. Chem. Soc.* vol. 60, p. 309 (1938).

The catalyst can further comprise effective amounts of promoter metal oxides selected from the group consisting of niobium, magnesium, calcium, scandium, yttrium, lanthanum, uranium, cerium, chromium, manganese, iron, cobalt, nickel, copper, zinc, aluminum, silicon, tin, tantalum, hafnium, zirconium, alkali metals (Cs, Rb, K, Na, Li) and mixtures thereof. The promoters and/or activators are readily introduced into the catalyst during deposition of vanadium and the reactive metal oxide sources on the catalyst precursor by admixture with the vanadium compounds during heating.

These promoter and activator compounds, however, should be at least partially soluble in any solvent medium used in the particular preparation in order to be best suited for combination with the vanadium components of the catalyst.

Typical compounds of zinc (illustrative of activators as a class) are metallic zinc, zinc oxide, zinc chloride, zinc bromide, zinc iodide, zinc formate, zinc nitrate or zinc acetate. Generally, phosphorus compounds are used which have as the cation an ion which is more volatile than the phosphate anion. Various compounds may be used, such as metaphosphoric acid, triphosphoric acid, pyrophosphoric acid, orthophosphoric acid, phosphorus pentoxide, phosphorus oxyiodide, ethyl phosphate, methyl phosphate, amine phosphate, phosphorus pentachloride, phosphorus trichloride, phosphorus oxybromide, and the like. The alkali metal may suitably be introduced by employing alkali metal compounds such as alkali metal salts with examples being lithium acetate, lithium bromide, lithium carbonate, lithium chloride, lithium hydroxide, lithium iodide, lithium oxide, lithium sulfate, lithium orthophosphate, lithium metavanadate, potassium sulfate, potassium chloride, potassium hydroxide, sodium chloride, sodium hydroxide, rubidium nitrate, cesium chloride and the like. Mixtures of two or more alkali metal compounds may be used, such as a mixture of lithium hydroxide and sodium chloride or a mixture of lithium chloride and potassium chloride. The preferred alkali metal elements are lithium, sodium and potassium, and mixtures thereof, with lithium being particularly preferred. The alkali metal compound will preferably be an alkali metal compound which either has a phosphate anion as the anion, that is a compound such as lithium phosphate, or a compound which has an anion which is more volatile than the phosphate anion.

These promoter metal oxides (or metal compounds which are sources for such oxides under calcination conditions) can be generally added to the catalyst solids by co-depositing on the calcined catalyst precursor with the vanadium. The amount of such promoter metal oxides which is employed in the catalyst can vary widely and will generally comprise from about 0.05 to 20 wt. % of the finally calcined catalyst, calculated as the corresponding promoter metal oxide. This will generally correspond to an atomic promoter metal oxide:titanium ratio of from 1:1 to 500:1, wherein the titanium content is calculated as titanium pentoxide.

The resulting finally calcined catalyst can be employed as such or deposited (as is preferred) on an inert catalyst carrier such as silicon carbide, silicon nitride, carborundum, steatite, alumina, alundum, and the like.

At some point in their preparation, the catalysts described herein preferably are formed into structures suitable for use in a reactor, although unshaped powder catalyst can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, Carbowax, Methocel ®, Avicel ® and graphite and the like. Extrusion or pelleting of the catalyst can be achieved by forming a wet paste.

Supported catalysts for use in either fixed or fluidized bed operations employ carriers including alumina, silica, silica gel, silica-alumina, silicon carbide, ceramic donuts, magnesium oxide, titania and titania-silica.

Spray dried catalysts can also be employed for fluidized bed operations.

A catalyst support, if used, provides not only the required surface for the catalyst, but gives physical strength and stability to the catalyst material. The carrier or support typically possesses a surface area of from about 0.01 to about 200 m²/g, preferably from about 0.05 to about 50 m²/g, and most preferably from about 0.1 to about 10 m²/g. A desirable form of carrier is one which has a rough enough surface to aid in retaining the catalyst adhered thereto during handling and under reaction conditions. The support may vary in size but generally is from about 2½ mesh to about 10 mesh in the Tyler Standard screen size. Alundum particles as large as ¼ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90% by weight, preferably from about 5 to about 80% by weight based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2½ to about 10 mesh size. The supports may be of a variety of shapes, of which the preferred shapes are cylinders or spheres.

The particle size of a supported or unsupported catalyst used in fluidized beds is quite shall, usually varying from about 10 to about 200 microns.

Inert diluents such as silica may be present in the catalyst, but the combined weight of the essential active ingredients of titanium dioxide and vanadium should preferably consist essentially of at least about 5 wt %, preferably at least about 15 wt %, based on the total weight of catalyst and support.

Shaping of unsupported catalyst can be conducted prior or subsequent to calcination of the Ti-deposited catalyst precursor. Preferably, shaping of the unsupported catalyst is conducted on the titanium dioxide catalyst solids prior to deposition of a Ti oxide source thereon. The point during which shaping with supports or carriers is conducted will vary with the type of support.

Solid supports, such as silica alumina, can be added to the reaction mixture during the formation of the catalyst precursor, or the above-described active catalyst ingredients can be sequentially deposited onto the solid support.

Vapor Phase Oxidation of Hydrocarbons

The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkanes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g., 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene-2 (cis or trans), 3-methylbutene-1, pentene-1, pentene-2, hexene-1, 3,3-dimethylbutene-1, 3-methyl-pentene-2, butadiene, pentadiene, cyclopentadiene, hexadiene, and mixtures thereof. It is also contemplated to use refinery streams rich in alkenes, particularly streams containing 70 percent or more butenes.

Representative examples of cycloalkanes, which can be methyl substituted, include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, or thiophene can be employed. Also suitable and readily available are naphthas obtained from paraffinic or naphthenic petroleum sources. Full boiling range naphthas (boiling within the range of about 35°–230° C.) can be used but it is preferred to use light naphtha cuts boiling within the range of about 35°–145° C. The naphthas usually contain about 5–15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane or isopentene to citraconic anhydride, maleic anhydride and a-carboxy maleic anhydride; pseudocumene to trimellitic anhydride; durene to pyromellitic anhydride; and orthoxylene and naphthalene to phthalic anhydride.

Preparation of Phthalic Anhydride

A preferred hydrocarbon feed for the catalyst of this invention for conversion to phthalic anhydride is orthoxylene, or an aromatic feedstream comprising a predominant amount orthoxylene and more preferably at least 10 mol. % orthoxylene. In the following discussion and exemplification, therefore, orthoxylene is used in most examples to demonstrate (but not to limit) the use of catalysts made by the process of this invention for producing phthalic anhydride. (It will be understood, for example, that naphthalene can also be employed as a hydrocarbon feed to prepare phthalic anhydride.)

The oxidation of orthoxylene to phthalic anhydride may be accomplished by contacting orthoxylene in low concentrations with oxygen in the presence of the described catalyst. Air is entirely satisfactory as a source of oxygen, but synthetic mixtures of oxygen and diluent gases, such as nitrogen, carbon dioxide and the like also may be employed. Air enriched with oxygen may be employed. The molecular oxygen-containing gas feed (e.g., air) is preferably preheated (e.g., to from 100°–300° C.) before introducing it into the reactor.

The gaseous feedstream to the oxidation reactors normally will contain air and typically from about 0.5 to about 10, preferably from about 1 to about 8, and most preferably from about 1.2 to about 5, mol. % orthoxylene. About 1.0 to about 1.9 mol. % of the orthoxylene in air is satisfactory for optimum yield of product for the process of this invention using a fixed bed reactor, and from about 2.5 to 4.0 mol. % orthoxylene using a fluidized bed. Although higher concentrations may be employed, explosive hazards may be encountered. Lower concentrations of orthoxylene less than about 1%, of course, will reduce the production rate obtained at equivalent flow rates and thus are not normally economically employed.

Flow rates of the gaseous feedstream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained. The hourly loading of the catalyst in a tube having a diameter of 22 mm and a length of 3 meters is generally from about 2000 to 6000 liters of air with about 20 to 150 g. of orthoxylene per 1000 liters of air.

A variety of reactors will be found to be useful and multiple tube heat exchanger type reactors are quite satisfactory. The tubes of such reactors may vary in diameter typically from about 20 to 50 mm, and the length may be varied from about 1 to 5 meters.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon steel, nickel, carbon-glass tubes such as Vycor and the like. Both carbon-steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the orthoxylene concentration. Under usual operating conditions, in compliance with the preferred procedure of this invention, the average bed temperature referred to herein as the reaction temperature, measured by thermocouples disposed in the reactor, is typically from about 300° to about 500° C., preferably from about 320° to about 440° C., and most preferably from about 330° to about 420° C. Under normal conditions, the temperature in the reactor ordinarily should not be allowed to go above about 525° C. for extended lengths of time because of decreased yields and possible deactivation of the novel catalyst of this invention.

The reaction may be conducted at atmospheric, superatmospheric or below atmospheric pressure, with pressure of from 1 to 20 psig being generally entirely suitable.

The phthalic anhydride may be recovered by a number of ways well known to those skilled in the art. For example, the recovery may be by direct condensation or by absorption in suitable media, with subsequent separation and purification of the phthalic anhydride. By-products such as tolualdehyde, phthalide, and maleic anhydride may also be formed, and can be separated from the phthalic anhydride by conventional means. If desired the purified phthalic anhydride can be reacted with an organic alcohol (such as an oxo-alcohol, e.g., isodecyl alcohol) to prepare phthalate esters which find use as plasticizers.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, the reactor used to test the catalyst is described as follows:

The reactor tube for the catalyst bed was fabricated from 316 stainless steel and had a ½-inch outside diameter, a wall thickness of 0.049 inch and a length of 12 inches. The bottom of the reactor tube was charged with 2 cc of 3 mm glass beads (VICOR ® beads), and then about 2 g. of unsupported catalyst, having an average particle size of about 0.5 mm and premixed with about 15 g (8 ml) of 0.55 mm glass beads (VICOR ® beads), was charged to the reactor as the catalyst bed. On top of the catalyst bed was then placed 2 cc of 3 mm glass beads (VICOR ® beads). A ⅛-inch stainless steel thermowell tube was provided down the center of the reactor tube, and a thermocouple was provided within the thermowell for measurement of catalyst bed temperatures along the length of the reactor. The reactor tube was immersed in a HITEC ® salt bath. The reactor inlet pressure as about 1 psig. The orthoxylene feed was caused to pass through the reactor tube in an upflow manner. Once a catalyst evaluation was started the reaction was continued for the longer of the selected run time or 8 hours. At the conclusion of each run, the catalyst, if to be used again, was kept under nitrogen purge at a temperature of from about 320° to 330° C. Analyses of reactor effluent gas were made at convenient time intervals by gas chromatography. Carbon balance was calculated according to the number of gram atoms of carbon in the reactor effluent to the gram atoms of carbon fed to the system.

Conversion of orthoxylene is calculated according to the following equation:

$$\% \text{ o-xylene conversion} = \frac{\text{g-moles of reacted o-xylene}}{\text{g-moles of o-xylene feed}} \times 100$$

Phthalic anhydride yield is calculated according to the following equation:

$$\% \text{ PAN yield} = \frac{\text{g-moles of PAN produced}}{\text{g-moles of o-xylene feed}} \times 100$$

The selectivity of phthalic anhydride is calculated according to the following equation:

$$\% \text{ selectivity to PAN} = \frac{\text{g-moles of PAN produced}}{\text{g-moles of o-xylene reacted}} \times 100$$

(% selectivity to intermediate oxidation products (e.g., tolualdehyde, phthalide) is calculated as shown above.)

In the Examples, the $TiO_2$ (Mobay) anatase charged was determined by atomic absorption analysis to contain about 0.15 wt. % K, 0.10 wt. % P, 0.10 wt. % Al and 0.16 wt. % Si (calculated as the respective elements) all of which are believed to be present as the corresponding metal oxides in the calcined catalysts prepared as described below. All Examples used $TiO_2$ (Mobay), 100% anatase, specific surface area of 9 $m^2/gm$, pore size of 150-250 um; $-60+-200$ mesh. All amounts are weight % unless otherwise indicated.

EXAMPLE 1

Catalyst Preparation

Catalyst A; 7% $V_2O_5$/3%$TiO_2$ on $TiO_2$ (anatase):

Step 1: To 4.38 gm titanium isopropoxid dissolved in 9 ml of toluene is added 37.88 gm titanium dioxide catalyst solids (i.e. $TiO_2$) under an $N_2$ atmosphere at room temperature. The thus-formed solution was heated with stirring at 120° C. to evaporate the toluene, followed by calcining in air at 500° C. for 16 hours. The resulting material was then sieved to $-100$ mesh powder. The thus-formed catalyst precursor comprised 3% $TiO_2$ on the titanium dioxide catalyst solids.

Step 2: A 38.49 gm portion of the powder produced in Step 1 was then contacted with 155 ml of an aqueous solution containing 2.90 gm $V_2O_5$, 6.37 gm oxalic acid and 14.48 gm formamide, followed by stirring in air at 65° C. to evaporate the majority of the water, drying in an oven (101 kPa) at 110° C. for 16 hours. The resulting solid was then calcined in a flowing oxygen gas stream at 450° C. for 2 hours, followed by crushing and screening to form $-20+40$ mesh particle size. The thus-formed catalyst was determined by calculation (based on the vanadium salt and the weight of the titanium dioxide particles) to comprise 7 wt % $V_2O_5$ on the $TiO_2$.

Catalyst B; 7% $V_2O_5$/3%$TiO_2$ on $TiO_2$ (anatase):

Step 1: A powder comprising 3% $TiO_2$ on $TiO_2$ was prepared following the procedure in Step 1 in preparing Catalyst A.

Step 2: A 20.55 gm sample of the thus-prepared powder was contacted with 83 ml of an aqueous solution of 1.547 gm $V_2O_5$, 7.73 gm formamide and 3.40 gm oxalic acid, followed by the procedure substantially as described in Step 2 of Catalyst A: stirring in air at 65° C. to evaporate the majority of the water, and drying in an oven (101 kPa) at 110° C. for 16 hours. The resulting solid was then calcined in a flowing oxygen gas stream at 450° C. for 2 hours, followed by crushing and screening to form $-20-+40$ mesh particle size. The thus-formed catalyst was determined by calculation (based on the vanadium salt and the weight of the titanium dioxide particles) to comprise 7 wt % $V_2O_5$ on the $TiO_2$.

Comparative Catalyst C; 7%$V_2O_5$/$TiO_2$ (anatase):

A catalyst is prepared following the procedure used to prepare Catalyst A of U.S. Pat. No. 4,582,911: To 40 ml of water is added 0.75 gm vanadium pentoxide, 1.65 gm oxalic acid and 3.75 gm formamide at room temperature with stirring to form vanadium oxalate, and this solution was then mixed with 10.0 gm titanium dioxide anatase powder (which were first dispersed in 20 ml of water). The resulting mixture was heated with stirring at 65° C. to evaporate the majority of the water, followed by drying in an oven (101 kPa) at 110° C. for 16 hours. The resulting solid was then calcined in a flowing oxygen gas stream at 450° C. for 2 hours, followed by crushing and screening to form $-20+40$ mesh particle sizer. The catalyst formed by the above impregnation procedure was determined by calculation (based on the vanadium salt and the weight of the titanium dioxide particles) to contain 7 wt. % $V_2O_5$ on the $TiO_2$.

EXAMPLE 2

Preparation of Phthalic Anhydride

Employing the reactor and process conditions indicated, the catalysts prepared as above were charged to the reactor tube in separate runs to determine their activity for the partial oxidation of orthoxylene to phthalic anhydride. From the data presented in the accompanying Table and the FIGURE, it can be seen that superior phthalic anhydride selectivities and yields are obtained at 100 mol % o-xylene conversion, employing the catalysts of the present invention.

TABLE I

| Catalyst (Run) | Temp. (°C.) | Run[1] Time (hrs) | o-xylene Conversion (mol %) | PAN Yield (mol %) | PAN Yield (wt. %) | Selectivities (mol %) to: PAN | Tol | Ph |
|---|---|---|---|---|---|---|---|---|
| Catalyst A | | | | | | | | |
| (Run 1) | 336 | 5.0 | 100 | 77.3 | 107.8 | 77.3 | 0 | 0 |
| | 333 | 3.5 | 98.9 | 76.7 | 107.1 | 77.6 | 0.2 | 0 |
| | 331 | 2.8 | 86.2 | 66.4 | 92.6 | 77.0 | 1.4 | 1.7 |
| | 327 | 4.6 | 70.0 | 51.0 | 71.2 | 72.9 | 3.2 | 2.3 |
| | 325 | 3.4 | 60.8 | 43.6 | 60.8 | 71.7 | 4.0 | 3.1 |
| | 323 | 2.8 | 53.8 | 36.2 | 50.5 | 67.3 | 5.1 | 4.8 |
| (Run 2)[2] | 322 | 6.0 | 100 | 77.0 | 107.4 | 77.0 | 0.0 | 0.0 |
| | 320 | 2.8 | 99.1 | 77.3 | 107.8 | 78.0 | 0.0 | 0.0 |
| | 318 | 4.5 | 96.7 | 76.7 | 107.0 | 79.3 | 0.5 | 0.0 |
| | 315 | 2.8 | 82.4 | 64.5 | 90.0 | 78.3 | 1.8 | 0.0 |
| | 314 | 5.2 | 72.4 | 56.1 | 78.3 | 77.5 | 2.5 | Trace |
| | 311 | 3.2 | 68.1 | 53.1 | 74.10 | 78.0 | 2.9 | Trace |
| | 308 | 2.9 | 51.6 | 38.0 | 53.0 | 73.6 | 4.3 | 3.1 |

TABLE I-continued

| Catalyst (Run) | Temp. (°C.) | Run[1] Time (hrs) | o-xylene Conversion (mol %) | PAN Yield (mol %) | PAN Yield (wt. %) | Selectivities (mol %) to: PAN | Tol | Ph |
| --- | --- | --- | --- | --- | --- | --- | --- | --- |
| (Run 3)[3] | 310 | 5.2 | 77.5 | 57.0 | 79.5 | 73.5 | 1.5 | 1.5 |
|  | 308 | 2.9 | 65.6 | 47.4 | 66.2 | 72.3 | 2.2 | 2.4 |
|  | 314 | 3.5 | 99.8 | 76.0 | 106.1 | 76.2 | 0.0 | 0.0 |
|  | 304 | 5.6 | 55.1 | 39.9 | 55.7 | 72.5 | 2.7 | 2.4 |
| Catalyst B |  |  |  |  |  |  |  |  |
|  | 344 | 6.8 | 100+ | 75.6 | 105.5 | 75.6 | 0.0 | 0.0 |
|  | 338 | 5.2 | 100 | 77.3 | 107.8 | 77.3 | 0.0 | 0.0 |
|  | 336 | 3.5 | 98.9 | 76.6 | 106.9 | 77.5 | Trace | 0.0 |
|  | 339 | 5.6 | 100 | 76.0 | 106.0 | 76.0 | 0.0 | 0.0 |
|  | 333 | 3.9 | 88.3 | 66.7 | 93.0 | 75.5 | 1.3 | 0.0 |
| Comparative Catalyst C |  |  |  |  |  |  |  |  |
|  | 343 | 5 | 98.4 | 73.4 | 102.4 | 74.6 | 0 | 0 |
|  | 339 | 8 | 100 | 73.6 | 102.7 | 73.6 | 0 | 0 |
|  | 321 | 3.6 | 60 | 44.8 | 62.5 | 74.6 | 3.8 | 2.4 |
|  | 326 | 2.6 | 74 | 57.3 | 79.9 | 77.4 | 2.2 | 1.3 |
|  | 332 | 2.4 | 94 | 72.0 | 100.4 | 76.6 | 0.6 | 0 |

Note:
"PAN"—phthalic anhydride; "Tol"—tolualdehyde; "Ph"—phthalide
[1] Vapor feed to reactor was 1.25 mol % o-xylene in air, and space velocity was 2760 hr$^{-1}$ unless otherwise stated.
[2] Vapor feed to reactor was 0.76 mol % o-xylene.
[3] Space velocity was 1380 hr$^{-1}$.

What is claimed is:

1. A process for the preparation of a carboxylic anhydride comprising reacting a hydrocarbon with molecular oxygen in the vapor phase, in the presence of a solid oxidation catalyst, said solid oxidation catalyst being obtained by the steps of:
   (a) forming a catalyst precursor by depositing on titanium dioxide catalyst solids in the anatase form, a continuous monolayer amount of at least one titanium oxide source which is convertible to titanium oxide upon calcining and titanium oxide source is deposited on said titanium dioxide catalyst solids in an amount sufficient to provide about 0.1 to 10 wt. % of titanium oxides, calculated as $TiO_2$, deposited on the titanium dioxide solids wherein the mole ratio of titanium present as a monolayer on the titanium dioxide catalyst solids to the titanium in the titanium dioxide solids is from about 0.0001 to about 0.111;
   (b) calcining said catalyst precursor under conditions sufficient to convert at least a portion of said titanium oxide source into titanium oxide;
   (c) depositing upon the calcined catalyst precursor at least a continuous monolayer amount of at least one vanadium oxide source which is convertible to vanadium oxide upon calcining;
   (d) calcining the catalyst solids formed in step (c) under conditions sufficient to convert at least a portion of said vanadium oxide source to vanadium oxide, said catalyst containing from about 0.7 to 50 wt. % vanadium oxides, calculated as $V_2O_5$ and the mole ratio of vanadium to titanium present in the calcined catalyst is from about 0.003 to 0.44 gram atoms of vanadium per gram atom of titanium.

2. The process according to claim 1 wherein said catalyst precursor is calcined in step (b) at a temperature of from about 150° to 750° C.

3. The process according to claim 2 wherein said calcining is effected for a time of from about 0.5 to 16 hours.

4. The process according to claim 1 wherein said vanadium oxide source comprises at least one member selected from the group consisting of vanadium halides, phosphates, oxides, carbonates, sulfates, alkoxides, nitrates, hydroxides, carboxylates and oxy halides.

5. The process according to claim 4 wherein said vanadium oxide source comprises at least one compound selected from the group consisting of vanadium pentoxide, ammonium metavanadate, vanadyl sulfate, vanadyl chloride, vanadyl dichloride, metavanatic acid, pyrovanatic acid, vanadium hydroxide, vanadyl oxalate and vanadyl carboxylates.

6. The process according to claim 1 wherein said catalyst, following calcination according to step (d), is characterized by a specific surface area of less than 50 square meters per gram.

7. The process according to claim 1 wherein said hydrocarbon comprises at least one member selected from the group consisting of orthoxylene and naphthalene, and wherein said carboxylic anhydride comprises phthalic anhydride.

8. The process according to claim 7 wherein said orthoxylene or naphthalene feed is passed to a reaction zone containing said solid oxidation catalyst at a mass flow rate of from about 20 to 150 grams per $Nm^3$ of air under vapor phase conditions, said reaction being effected at a temperature of from about 200° to 500° C.

9. The process according to claim 1 wherein said hydrocarbon comprises durene and wherein said carboxylic anhydride comprises pyromellitic dianhydride.

10. The process according to claim 9 wherein said durene is passed to a reaction zone containing said solid oxidation catalyst under the vapor phase reaction conditions and at a durene feed rate of from about 5 to 100 grams per $Nm^3$ of air, and said reaction is effected at a temperature within the range of from about 200° to 500° C.

11. The process according to claim 1 wherein said vanadium oxide source is deposited upon said calcined catalyst precursor in an amount sufficient to provide at least $N_{min}$ grams of $V_2O_5$, wherein $$N_{min} = (G) \times (A) \times (0.0007)$$

wherein "G" is the grams of said calcined catalyst precursor and "A" is the specific surface area of said calcined catalyst precursor.

12. The process according to claim 11 wherein said vanadium oxide source is deposited on said calcined catalyst precursor in an amount sufficient to provide at least about 1.7 $N_{min}$ grams of $V_2O_5$.

* * * * *